US00PP17680P2

(12) United States Plant Patent

Sakazaki

(10) Patent No.: US PP17,680 P2

(45) Date of Patent: May 1, 2007

(54) *CALIBRACHOA* PLANT NAMED 'USCALI53M'

(50) Latin Name: ***Calibrachoa* sp.**
Varietal Denomination: USCALI53M

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 11/273,564

(22) Filed: Nov. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Calibrachoa* plant named 'USCALI53M', characterized by its semi-upright to cascading plant habit; freely branching habit; freely flowering habit; relatively large yellow and dark red bi-colored flowers; and tolerance to rain and low and high temperatures.

1 Drawing Sheet

Botanical designation: *Calibrachoa* sp.
Cultivar denomination: 'USCALI53M'.

BACKGROUND OF THE INVENTION

The present Invention relates to a new and distinct cultivar of *Calibrachoa* plant, botanically known as *Calibrachoa* sp., and hereinafter referred to by the cultivar name 'USCALI53M'.

The new *Calibrachoa* is a naturally-occurring branch mutation of a proprietary selection of *Calibrachoa* sp., identified as code number SB53, not patented. The new *Calibrachoa* was discovered and selected by the Inventor on Jun. 14, 2003 from within a population of plants of the parent selection in a controlled environment in Gensingen, Germany.

Asexual reproduction of the new cultivar by terminal cuttings in a controlled environment in Gensingen, Germany since Jul. 20, 2003, has shown that the unique features of this new *Calibrachoa* are stable and reproduced true to type in successive generations.

SUMMARY OF THE INVENTION

Plants of the cultivar USCALI53M have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USCALI53M'. These characteristics in combination distinguish 'USCALI53M' as a new and distinct cultivar of *Calibrachoa:*

1. Semi-upright to cascading plant habit.
2. Freely branching habit.
3. Freely flowering habit.
4. Relatively large yellow and dark red bi-colored flowers.
5. Good weather tolerance; tolerant to rain and low and high temperatures.

Plants of the new *Calibrachoa* differ primarily from plants of the parent selection primarily in flower color as plants of the parent selection have dark red purple-colored flowers.

Plants of the new *Calibrachoa* can be compared to plants of the cultivars Million Bells Terra Cotta, not patented, and Million Bells Cracklin Fire, not patented. In side-by-side comparisons conducted in Gensingen, Germany, plants of the new *Calibrachoa* had larger flowers than plants of the cultivars Million Bells Terra Cotta and Million Bells Cracklin Fire.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet is a close-up view of typical flowers and leaves of 'USCALI53M'.

The photograph at the bottom of the sheet comprises a side perspective view of a typical plant of 'USCALI53M' grown in a container.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers were used for the aforementioned photographs and following description. Plants were about two months from planting rooted cuttings. Plants were grown under conditions which closely approximate commercial production conditions during the summer in Bonsall, Calif. in an outdoor nursery. During the production period, day temperatures ranged from 21° C. to 35° C. and night temperatures ranged from 10° C. to 18° C.

Botanical classification: *Calibrachoa* sp. cultivar USCALI53M.

Parentage: Naturally-occurring branch mutation of a proprietary selection of *Calibrachoa* sp. identified as code number SB53, not patented.

Propagation:

*Type cutting.*—Terminal vegetative cuttings.

*Time to initiate and develop roots.*—Summer: About three weeks at 20° C. Winter: About four weeks at 20° C.

*Root description.*—Fine, freely-branching; whitish in color.

Plant description:

*Form.*—Annual flowering plant; initially upright to semi-upright, eventually cascading; uniformly mounded appearance.

*Usage.*—Appropriate for hanging baskets, window boxes and patio containers.

*Plant height* (*from soil level to top of plant plane*).—About 16 cm.

*Plant diameter.*—About 64 cm.

*Growth rate.*—Moderate to rapid growth rate; vigorous.

*Branching habit.*—Freely branching, about ten primary branches per plant each with multiple secondary branches; pinching is typically not required.

*Lateral branch description.*—Length: About 36 cm. Diameter: About 4 mm. Internode length: About 1.7 cm. Texture: Pubescent. Color: 144B.

*Foliage description.*—Arrangement: Alternate until flowering, then opposite; simple. Length: About 3 cm. Width: About 1.1 cm. Shape: Elliptical. Apex: Rounded. Base: Attenuate. Margin: Entire. Texture, upper and lower surfaces: Slightly pubescent and rough. Venation pattern: Pinnate; arcuate. Color: Developing and fully expanded foliage, upper surface: 147A. Developing and fully expanded foliage, lower surface: 147B. Venation, upper surface: 147B. Venation, lower surface: 147C. Petiole: Length: About 5 mm. Diameter: About 2 mm. Texture, upper and lower surfaces: Pubescent. Color, upper surface: 147B. Color, lower surface: 147C.

Flower description:

*Flower type and habit.*—Flowers face upright or outward; single, relatively large, axillary; salverform. Flowers persistent. Freely flowering habit, about 28 flowers and flower buds per lateral stem. Flowers not fragrant. Flowers face upright and bending outwardly.

*Natural flowering season.*—April through September in Southern California; flowering continuous during this period.

*Time to flower.*—Early flowering; plants begin flowering about four to six weeks after planting.

*Flower longevity on the plant.*—About seven to ten days.

*Flower size.*—Diameter: About 3 cm. Depth: About 2.4 cm. Tube length: About 2 cm. Flower throat diameter: About 5 mm by 8 mm. Flower tube diameter: About 2.5 mm.

*Flower buds.*—Length: About 2 cm. Diameter: About 5 mm. Shape: Elongated oblong. Color: 10C.

*Corolla.*—Arrangement/appearance: Single whorl of five petals, fused into flared trumpet. Petal length from throat: About 1.2 cm. Petal width: About 1.3 cm. Petal shape: Roughly obovate. Petal apex: Nearly round with a very shallow central point. Petal margin: Entire. Petal texture, upper surface: Smooth, glabrous; satiny. Petal texture, lower surface: Slightly pubescent. Throat texture: Smooth, glabrous. Tube texture: Pubescent. Color: Petal, when opening, upper surface: Ground color, 12C; thin longitudinal stripes, 45B. Petal, when opening, lower surface: 12D. Petal, opened flower, upper surface: Ground color, 13A; longitudinal stripes, sectors and/or random flecks, Between 46B to 60A; venation, 199B. Petal, opened flower, lower surface: Ground color, 12D overlain with 61B to 61C; venation, 183C. Flower throat (inside): 14A; venation, 183B. Flower tube (outside): 12C; venation, 183A.

*Sepals.*—Arrangement/appearance: Single whorl of five sepals, fused at base; star-shaped. Length: About 8 mm. Width: About 2 mm. Shape: Narrowly lanceolate. Apex: Acute. Margin: Entire. Texture, upper and lower surfaces: Pubescent. Color, upper and lower surfaces: 146A.

*Peduncles.*—Length: About 2.2 cm. Width: About 1 mm. Strength: Strong. Angle: About 45° to 60° from the stem. Texture: Pubescent. Color: 146C.

*Reproductive organs.*—Stamens: Quantity: Five per flower. Anther shape: Oval. Anther length: About 1 mm. Anther color: 10A. Pollen amount: Scarce. Pollen color: 10A. Pistils: Quantity: One per flower. Pistil length: About 1.5 cm. Stigma shape: Oval. Stigma color: 148A. Style length: About 1.2 cm. Style color: 145C. Ovary color: 145A.

*Seed/fruit.*—Seed and fruit production has not been observed.

Disease/pest resistance: Plants of the new *Calibrachoa* have not been noted to be resistant to pathogens and pests common to *Calibrachoas.*

Weather/temperature tolerance: Plants of the new *Calibrachoa* are tolerant to rain and wind and have been observed to tolerate temperatures from 1° C. to 41° C.

It is claimed:

1. A new and distinct cultivar of *Calibrachoa* plant named 'USCALI53M', as illustrated and described.

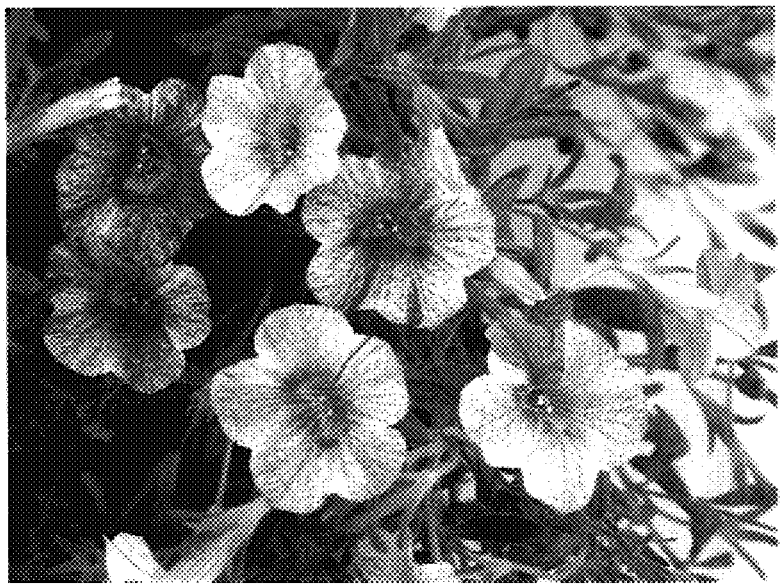
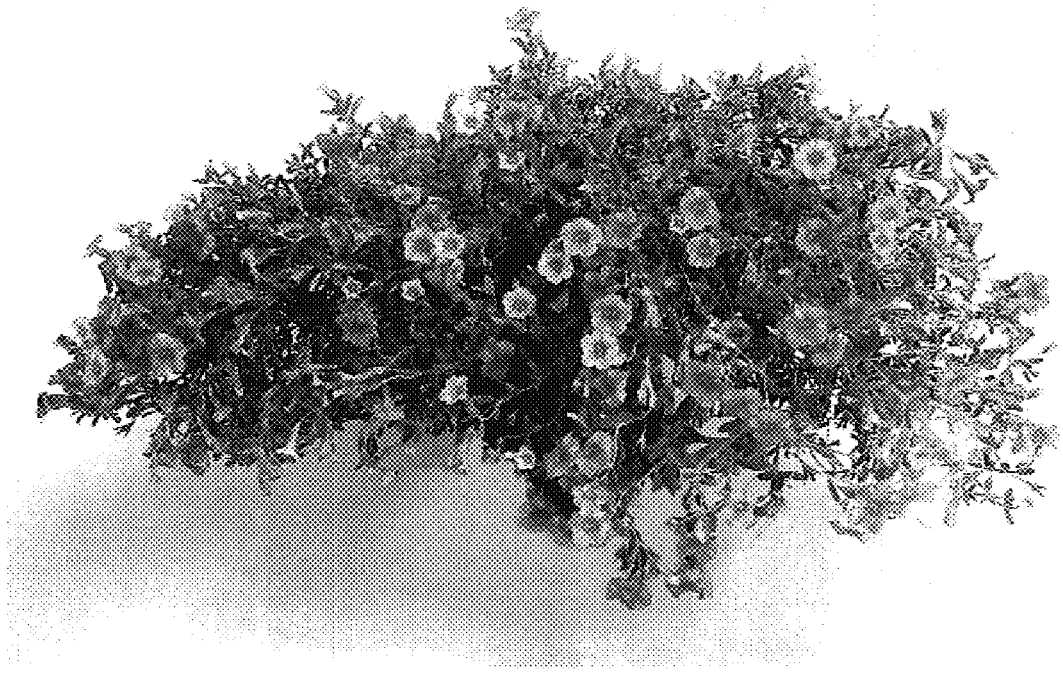

* * * * *